United States Patent [19]

Jones

[11] 4,420,480

[45] Dec. 13, 1983

[54] HEXAHYDRONAPHTH[1,2-B]-1,4-OXAZINES

[75] Inventor: James H. Jones, Blue Bell, Pa.

[73] Assignee: Merck & Co., Inc., Rahway, N.J.

[21] Appl. No.: 412,748

[22] Filed: Aug. 30, 1982

Related U.S. Application Data

[63] Continuation-in-part of Ser. No. 323,349, Nov. 20, 1981, abandoned.

[51] Int. Cl.$^3$ .................. A61K 31/335; C07D 498/00
[52] U.S. Cl. ............................ 424/248.4; 424/248.57; 424/248.58; 544/99; 544/101
[58] Field of Search ............... 544/99, 101; 424/248.4, 424/248.57, 248.58

[56] References Cited

U.S. PATENT DOCUMENTS 4,238,486  12/1980  Jones ........................... 424/248.4

OTHER PUBLICATIONS

Neuman et al., *J. Org. Chem.*, 28, 116 (1963).
Chem. Abstr., 85:177339y, Dalev et al.
Craig et al., *J. Org. Chem.*, 39, 1669 (1974).

*Primary Examiner*—Richard Raymond
*Attorney, Agent, or Firm*—William H. Nicholson; Mario A. Monaco

[57] ABSTRACT

Hexahydronaphth[1,2-b]-1,4-oxazines have dopaminergic activity and display $\alpha_2$-adrenergic receptor antagonism. They are useful in the treatment of parkinsonism, depression and hypertension. An important method of preparation is by ring closure of the appropriate 2-chloroacetamidotetrahydronaphthalen-1-ol and reduction of the resulting cyclic amide carbonyl group.

32 Claims, No Drawings

HEXAHYDRONAPHTH[1,2-b]-1,4-OXAZINES

This is a continuation-in-part of copending application Ser. No. 323,349, filed Nov. 20, 1981, now abandoned.

BACKGROUND OF THE INVENTION

The tetracyclic ergoline type of compound (U.S. Pat. No. 3,968,111) has pharmaceutical activity, and the indolobenzoxazines (U.S. Pat. No. 4,238,486) in which the D-ring of the ergolines is a tetrahydrooxazine have antihypertensive and antiparkinson activity.

SUMMARY OF THE INVENTION

This invention is concerned with trans-1a,2,3,4a,5,6-hexahydronaphth[1,2-b]-1,4-oxazine and derivatives of structural formula:

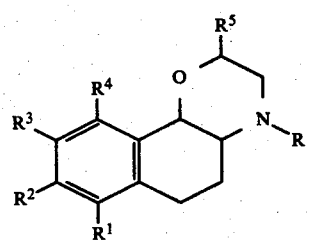

I and pharmaceutically acceptable salts thereof. The novel compounds demonstrate the dopaminergic activity of antiparkinson and antihypertensive agents. Some of the novel compounds are also $\alpha_2$-adrenergic receptor antagonists and hence antidepressant.

It is, therefore, an object of this invention to provide novel compounds of formula I; novel processes for their preparation; novel pharmaceutical formulations comprising one or more of the novel compounds as active ingredient; and novel methods of treating Parkinsonism, hypertension and depression by administration of a novel compound to a patient in need of such treatment.

DETAILED DESCRIPTION OF THE INVENTION

The novel compounds of this invention have general structural formula I which is used herein to represent the trans-isomers only.

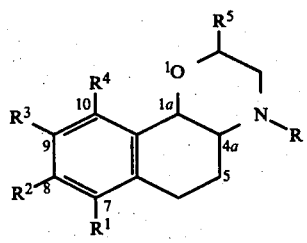

I or a pharmaceutically acceptable salt thereof, wherein
R is (a) hydrogen;
(b) $C_{1-4}$ alkyl either branched or straight chain, especially ethyl or propyl;
(c) $C_{2-5}$ alkenyl, especially allyl; or
(d) phenyl-$C_{1-4}$ alkyl especially benzyl; and
$R^1$, $R^2$, $R^3$ and $R^4$ are independently selected from
(a) hydrogen,
(b) $C_{1-4}$ alkyl, especially methyl,
(c) halo, such as fluoro, chloro or bromo,
(d) —$OR^6$ wherein $R^6$ is
(1) hydrogen
(2) $C_{1-3}$ alkyl, especially methyl,
(3) phenyl-$C_{1-3}$ alkyl, especially benzyl,

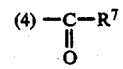

(4)

wherein $R^7$ is
(i) $C_{1-6}$ alkyl, either straight or branched chain, such as methyl, t-butyl, or the like,
(ii) $C_{3-6}$ cycloalkyl, such as cyclopropyl, cyclohexyl or the like,
(iii) benzenoid aryl-$C_{1-3}$ alkyl, especially phenyl-$C_{1-3}$ alkyl wherein the aryl group is unsubstituted or substituted with one or more groups such as halo, $C_{1-3}$ alkyl, or $C_{1-3}$ alkoxy,
(iv) heteroaryl-$C_{1-3}$alkyl, such as pyridyl- or furyl-$C_{1-3}$ alkyl,
(v) benzenoid aryl especially phenyl, either unsubstituted or substituted with one or more groups such as halo, $C_{1-3}$ alkyl, or $C_{1-3}$ alkoxy,
(vi) heteroaryl such as pyridyl or furyl, and
(vii) —$NR^8R^9$, wherein $R^8$ and $R^9$ are independently hydrogen or $C_{1-3}$ alkyl, or $R^8$ and $R^9$ may be joined together to form a heterocycle with the nitrogen to which they are attached such as piperidinyl, morpholinyl, piperazinyl, or N—$C_{1-3}$alkyl-piperazinyl, and $R^5$ is hydrogen, $C_{1-3}$ alkyl or phenyl.

A preferred embodiment is that wherein R is $C_{1-4}$ alkyl especially ethyl or n-propyl, and one or more of $R^1$, $R^2$, $R^3$ and $R^4$ is hydroxy, methoxy, acetoxy or pivaloyloxy especially in the 9-position.

The novel compounds of this invention have two asymmetric carbon atoms, 4a and 1a, where the morpholino ring is fused to the tetrahydronaphthalene ring. This invention includes stereoisomers in which these asymmetric centers are in a trans conformation. The invention further includes the individual enantiomers and mixtures thereof including the racemate.

Both enantiomers and mixtures thereof have dopaminergic activity, but the (+)-trans compound is much preferred for that utility. On the other hand, the (−)-trans enantiomer is preferred for $\alpha_2$-adrenergic receptor blockade.

The pure optical antipodes can be prepared from the appropriate optically pure intermediates or by resolution of the final racemic product.

The pharmaceutically acceptable salts of the novel compound of this invention are acid addition salts formed from a novel compound and an organic or inorganic acid recognized by the art as providing a pharmaceutically acceptable acid addition salt, such as hydrochloride, hydrobromide, dihydrogen phosphate, sulfate, citrate, pamoate, pyruvate, napsylate, isethionate, maleate, fumarate, or the like.

These salts are readily prepared by mixing solutions of equimolecular amounts of the free base compound and the desired acid in suitable solvents such as water, alcohols, ether or chloroform, followed by recovery of the product by collecting the precipitated salt or evaporation of the solvent.

A novel process for preparing the novel compounds is another embodiment of this invention and is represented as follows:

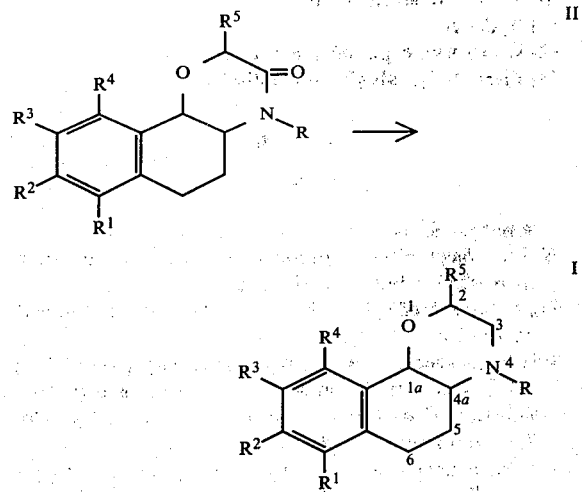

The novel process comprises the reduction of the oxazinone, II, with a complex metal hydride such as lithium aluminum hydride in an inert organic solvent such as an ether, for example, tetrahydrofuran, 1,2-dimethoxyethane, tetrahydropyran, or the like at a temperature between about 0° C. and 100° C. Operating procedures normally involve slow addition of the cyclic amide to the reducing agent at room temperature or below, followed by heating to an elevated temperature within the stated range, preferably, the reflux temperature of the solvent, for about ½ to about 8 hours usually about 4 hours.

If, in the novel process of this invention, the nitrogen substituent, R, is hydrogen, and it is desired that it be one of the other substituents within the definition of R the product from the foregoing reaction may be treated with the appropriate alkylating agent of formula:

R—X wherein R is as defined earlier and X is a suitable leaving group such as, iodo, bromo, chloro, mesylate, tosylate, or the like. The alkylation is conducted in an organic solvent such as DMF, DMSO, or THF, preferably DMF, at about 10° to about 100° C. until the reaction is substantially complete; usually about 3 to 10 hours.

If one or more of $R^1$, $R^3$ or $R^4$ is alkoxy, it or they may be converted to hydroxy, if desired, by heating at about 150°–250° C. in excess pyridine hydrochloride for about 3 to 8 hours. Alternatively, the deetherification can be accomplished by treatment with boron tribromide ($BBr_3$) or aluminum chloride ($AlCl_3$) in an inert organic solvent such as petroleum ether, or hexane, or a chlorinated hydrocarbon such as methylene chloride, tetrachloroethane or the like, between room temperature and reflux temperature for 3 to about 8 hours.

Also, if $R^1$, $R^2$, $R^3$ or $R^4$ is benzyloxy or substituted benzyloxy it or they can be converted to hydroxy by hydrogenolysis with a noble metal catalyst such as palladium, platinum, or platinum oxide, with or without a carrier such as carbon, or the like, preferably palladium on carbon, in an inert organic solvent such as $C_{1-3}$ alkanol, an ethereal solvent such as tetrahydrofuran, 1,2-dimethoxyethane, or the like, or mixtures thereof. The reaction is conducted at or near room temperature such as 15°–30° C. until hydrogen uptake ceases or the requisite amount of hydrogen is consumed.

In those compounds wherein $R^1$, $R^2$, $R^3$ or $R^4$ is

they are prepared by treatment of the corresponding hydroxy compound with the appropriate acid anhydride

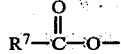

acid chloride

or the like, in the presence of an acylation catalyst such as pyridine, 4-dimethylaminopyridine or 4-pyrolidinopyridine. Temperatures from about 15° C. to 100° C. are used until the reaction is substantially complete.

A third embodiment of this invention is a pharmaceutical formulation comprising one of the novel compounds as active ingredient. It may be in any art recognized form suitable for oral use, such as tablets, troches, lozenges, aqueous or oil suspensions, dispersible powders, or granules, emulsions, hard or soft capsules, syrups, or elixirs. For intravenous, intramuscular and subcutaneous use the pharmaceutical compositions may be in any art recognized form of a sterile injectable preparation such as a sterile aqueous or oleaginous solution or suspension. The amount of active ingredient incorporated in a unit dosage of the above described pharmaceutical compositions may be from 1 to 400 mg, and preferably from 5 to 250 mg.

Other embodiments of this invention are the treatment of hypertension and/or parkinsonism with a compound of Formula I with zero or positive optical activity. The route of administration can be oral, rectal, intravenous, intramuscular, or subcutaneous. Doses of 0.1 to 20 mg/kg/day and preferably of 0.5 to 10 mg/kg/day of active ingredient are generally adequate, and if preferred it can be administered in divided doses given two to four times daily.

In the treatment of Parkinsonism, this invention also includes the coadministration of a compound of Formula I with zero or positive optical rotation with an art-recognized antiparkinsonism agent such as SINEMET ® (Merck & Co., Inc., Rahway, N.J.), each agent being administered in a dose comparable to that recommended for use as though it were the sole therapeutic agent. The coadministration is accomplished either by administration of the two agents separately at approximately the same time or by administration of a single unit dosage form comprising the combined agents such as: 10 mg of a compound of Formula I with zero or positive optical rotation; 100 mg of 1-dopa; and 10 mg of carbidopa. The coadministration is particularly useful when, as frequently happens, parkinsonism symptoms break through despite a history of successful treatment with SINEMET ® or other art recognized antiparkinsonism agent.

A further method of treatment, comprising another embodiment of this invention, is the treatment of depression with a compound of Formula I with zero or negative optical activity. Doses and modes of administration comparable to those described above are satisfactory for this novel method of treatment.

It is to be noted that the precise unit dosage form and dosage level depend upon the requirements of the individual being treated, and consequently are left to the discretion of the therapist.

EXAMPLE 1

Trans-1a,2,3,4a,5,6-hexahydro-4H-naphth[1,2-b]-1,4-oxazine hydrochloride

Step A: Preparation of 2-chloroacetamido-3,4-dihydronaphthalen-1(2H)-one

To a stirred solution of sodium bicarbonate (4.0 g) in water (50 ml) layered with ethyl acetate (200 ml) was added solid 2-amino-3,4-dihydronaphthalen-1(2H)-one hydrochloride (4.0 g, 2 mmol). After the solid had dissolved chloroacetylchloride (1.6 ml, 2 mmol) was added dropwise over 10 minutes. After stirring for 1 hr, the ethyl acetate layer was separated, washed with brine and dried over $Na_2SO_4$. Evaporation afforded 2.7 g (57%) of a dark solid; m.p. 118°–122° C. The product was purified by chromatography on silica using ethyl acetate: hexane (1:1 v/v) to elute, m.p. 121°–123° C.

Step B: Preparation of trans-2-chloroacetamido-1,2,3,4-tetrahydronaphthalen-1-ol To a solution of 2-chloroacetamido-3,4-dihydronaphthalen-1(2H)-one (2.3 g, 1 mmole) in ethanol (50 ml) and chloroform (20 ml) was added sodium borohydride (500 mg) in portions. After 1 hr, several drops of acetic acid were added to destroy excess sodium borohydride. The mixture was poured into water (150 ml) and the product was extracted into chloroform. The chloroform was separated, dried ($Na_2SO_4$) and evaporated to yield 1.7 g (71%) of a white solid m.p. 126°–130° C. After recrystallization from butylchloride it had m.p. 136°–138° C.

Step C: Preparation of trans-1a,2,4,4a,5,6-hexahydronaphth[1,2-b]-1,4-oxazin-3-one To a suspension of NaH (2.4 g, 53% mineral oil) in DMF (24 ml) was added a solution of trans-2-chloroacetamido-1,2,3,4-tetrahydronaphthalen-1-ol (5.5 g, 2.3 mmole). The reaction mixture was stirred at room temperature for 3 hr, some ethanol was added to destroy excess NaH and the reaction mixture was poured into water (150 ml). The resulting solid was filtered and dried to yield 3.1 g (71%) of product, m.p. 225° C. (dec). After recrystallization from butyl chloride it had m.p. 232°–235° C. (dec).

Step D: Preparation of trans-1a,2,3,4a,5,6-hexahydro-4H-naphth[1,2-b]-1,4-oxazine hydrochloride To a stirred suspension of $LiAlH_4$ (2.0 g) in THF (100 ml) was added a solution of trans-1a,2,4,4a,5,6-hexahydronaphth[1,2-b]-1,4-oxazin-3-one (2.4 g, 1.2 mmole) in THF (250 ml). The reaction mixture was heated at reflux for 4 hrs, cooled in an ice bath, and ethanol was added to destroy excess $LiAlH_4$. Rochell salt (100 ml of a 20% (w/v aqueous) solution) was added and the mixture was extracted with ethyl acetate ($3 \times 300$ ml). The ethyl acetate layer was dried ($Na_2SO_4$) treated with decolorizing carbon, filtered, and evaporated to a red oil. The oil was dissolved in 20 ml of 1:1 (v/v) acetone-ether and several ml of methanolic hydrochloric acid was added. The resulting solid was filtered and dried to yield 2.5 g of product, m.p. 290° C. (dec).

EXAMPLE 2

Trans-1a,2,3,4a,5,6-hexahydro-7-methoxy-4H-naphth[1,2-b]-1,4-oxazine hydrochloride Employing the procedures substantially as described in Example 1, Steps A through D, but substituting for the starting material used therein an equimolecular amount of 2-amino-5-methoxy-3,4-dihydronaphthalen-1(2H)-one hydrochloride, there were produced in sequence:

Step A: 2-chloroacetamido-5-methoxy-3,4-dihydronaphthalen-1(2H)-one, m.p. 147°–149° C.

Step B: trans-2-chloroacetamido-5-methoxy-1,2,3,4-tetrahydronaphthalen-1-ol, m.p. 125°–128° C.

Step C: trans-1a,2,4,4a,5,6-hexahydro-7-methoxynaphth[1,2-b]-1,4-oxazin-3-one, m.p. 294°–295° C.

Step D: trans-1a,2,3,4a,5,6-hexahydro-7-methoxy-4H-naphth[1,2-b]-1,4-oxazine hydrochloride, m.p. 260° C.

Employing the procedure substantially as described in Example 1, Steps A through D but substituting for the starting materials used in Step A thereof an equimolecular amount of each of the substituted 2-amino-3,4-dihydronaphthalen-1(2H)-ones described in Table I and the $\alpha$-$R^5$-chloroacetyl chlorides also described in Table I there are produced the respective substituted trans-1a,2,3,-4a,5,6-hexahydronaphth[1,2-b]-1,4-oxazines also described in Table I in accordance with the following reaction sequence:

TABLE I

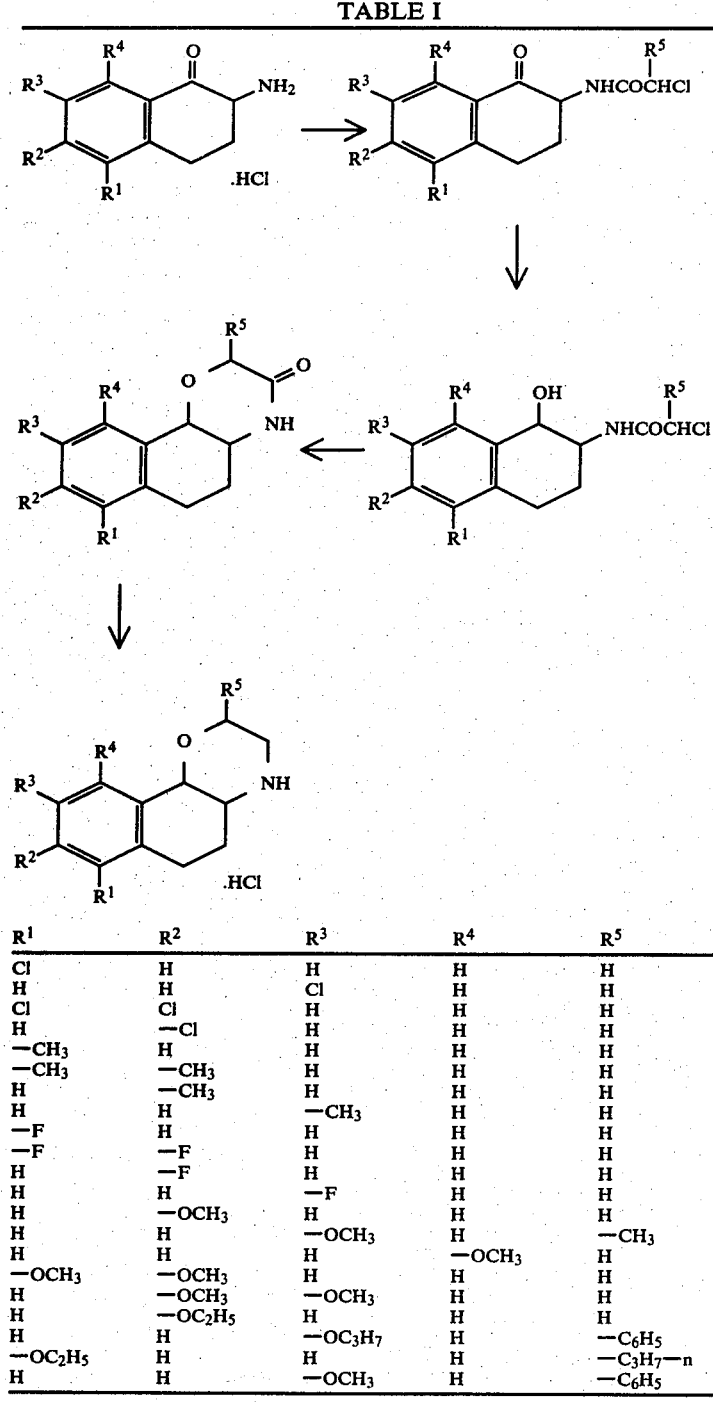

| R¹ | R² | R³ | R⁴ | R⁵ |
|---|---|---|---|---|
| Cl | H | H | H | H |
| H | H | Cl | H | H |
| Cl | Cl | H | H | H |
| H | —Cl | H | H | H |
| —CH₃ | H | H | H | H |
| —CH₃ | —CH₃ | H | H | H |
| H | —CH₃ | H | H | H |
| H | H | —CH₃ | H | H |
| —F | H | H | H | H |
| —F | —F | H | H | H |
| H | —F | H | H | H |
| H | H | —F | H | H |
| H | —OCH₃ | H | H | H |
| H | H | —OCH₃ | H | —CH₃ |
| H | H | H | —OCH₃ | H |
| —OCH₃ | —OCH₃ | H | H | H |
| H | —OCH₃ | —OCH₃ | H | H |
| H | —OC₂H₅ | H | H | H |
| H | H | —OC₃H₇ | H | —C₆H₅ |
| —OC₂H₅ | H | H | H | —C₃H₇—n |
| H | H | —OCH₃ | H | —C₆H₅ |

EXAMPLE 3

Trans-1a,2,3,4,a,5,6-hexahydro-4-benzyl-4H-naphth[1,2-b]-1,4-oxazine hydrochloride hemihydrate

Step A: Preparation of 2-benzamido-3,4-dihydronaphthalen-1(2H)-one

A solution of N-benzoyl homophenylalanine (4.4 g, 1.66 mmole) in acetic anhydride (60 ml) was heated on the steam bath for ½ hr. The solvent was removed in vacuo, the resulting oil was dissolved in CS₂ and then added to a suspension of AlCl₃ (6.2 g, 4.6 mmoles) in CS₂ (60 ml). This mixture was heated at reflux for 1 hr, the solvent was removed in vacuo and ice was added to the residue. The reaction mixture was extracted with ethyl acetate, the ethyl acetate layer was washed with brine, dried over Na₂SO₄ and evaporated to dryness to afford 3.6 g (88%) of product, m.p. 175° C. After recrystallization from toluene it had m.p. 175°–178° C.

Step B: Preparation of trans-2-benzylamino-1,2,3,4-tetrahydronaphthalen-1-ol A solution of 2-benzamido-3,4-dihydronaphthalen-1(2H)-one (3.0 g, 1.1 mmole) in THF (150 ml) was added dropwise to a suspension of LiAlH₄ (2.0 g) in THF (50 ml). The reaction was heated at reflux for 2 hr and then cooled to room temperature. Enough ethanol was added to destroy excess LiAlH₄ followed by 150 ml of Rochell's salt solution (20%). The resulting mixture was extracted with ethyl acetate, the ethyl acetate layer was washed with brine and dried over Na₂SO₄. Evaporation of the solvent afforded 2.5 g (88%) of the product, m.p. 110°–114° C. After recrystallization from cyclohexane it had m.p. 112°–115° C.

Step C: Preparation of trans-1a,2,4,4a,5,6-hexahydro-4-benzylnaphth[1,2-b]-1,4-oxazin-3-one A bicarbonate solution (2.0 g in 75 ml of H₂O) was layered with an ethyl acetate solution (100 ml) containing trans-2-benzylamino-1,2,3,4-tetrahydronaphthalen-1-ol (2.0 g, 0.8 mmole), and the whole was stirred rapidly while chloroacetyl chloride (0.89 g, 0.8 mmole) was added dropwise. After 0.5 hr the ethyl acetate layer was separated, dried over Na₂SO₄ and evaporated. The resulting light purple solid was dissolved in DMF (10 ml) and added to a suspension of NaH (0.5 g of 53% mineral oil) in DMF (15 ml). After 1 hr the reaction mixture was poured into water (150 ml). The solid that separated was filtered and dried to yield 1.8 g (78%) of product, m.p. 185° C. After recrystallization from butyl chloride it had m.p. 185°–187° C.

Step D: Preparation of trans-1a,2,3,4a,5,6-hexahydro-4-benzyl-4H-naphth[1,2-b]-1,4-oxazine hydrochloride hemihydrate This reaction was carried out substantially as described in Example 1, Step D using trans-1a,2,4,4a,5,6-hexahydro-4-benzylnaphth[1,2-b]-1,4-oxazin-3-one as the starting material. There was obtained a 64% yield of product, m.p. 262°–265° C. (dec.).

EXAMPLE 4 trans-1a,2,3,4a,5,6-hexahydro-4-allyl-4H-naphth[1,2-b]-1,4-oxazine hydrochloride To a solution of trans-1a,2,3,4a,5,6-hexahydro-4H-naphth[1,2-b]-1,4-oxazine (1.0 g, 0.52 mmole) (Example 1, Step D) in DMF (15 ml) was added K₂CO₃ (1.1 g) and allyl bromide (0.95 g, 0.79 mmoles). The reaction mixture was stirred at room temperature for 6 hrs, and then concentrated in vacuo to a small volume. The reaction was diluted with water (40 ml) and extracted with ether (3×100 ml). The ether layer was washed with brine, dried over Na₂SO₄ and filtered. Ethanolic hydrochloric acid was added and the salt separated to give 0.77 g (55%) of product, m.p. 187°–192° C.

Employing the procedure substantially as described in Example 4 but substituting for the naphthoxazine and allyl bromide used therein, equimolecular amounts of the naphthoxazines and alkyl halides (R—X) described in Table II, there were produced the N-alkyl-naphthoxazines, also described in Table II in accordance with the following reaction:

TABLE II

| X | R | R¹ | R² | R³ | R⁴ | HCl salt m.p. (°C.) |
|---|---|---|---|---|---|---|
| Br | n-C₃H₇— | H | H | H | H | 259–261 |
| Br | C₂H₅— | —OCH₃ | H | H | H | 279–284 |
| Br | CH₂=CHCH₂— | —OCH₃ | H | H | H | 245–246 |

Similarly prepared are the compounds described in Table III.

TABLE III

| R | R¹ | R² | R³ | R⁴ | R⁵ |
|---|---|---|---|---|---|
| CH₃— | H | H | H | H | H |
| CH₃— | —OCH₃ | H | H | H | H |
| C₆H₅CH₂— | H | H | H | H | H |
| C₆H₅CH₂— | —OCH₃ | H | H | H | H |
| C₂H₅— | —Cl | H | H | H | H |
| C₂H₅— | Cl | —Cl | H | H | H |
| C₂H₅— | H | —CH₃ | H | H | H |
| C₂H₅— | H | H | —CH₃ | H | —CH₃ |
| C₂H₅— | —F | —F | H | H | H |
| C₃H₇ | —OCH₃ | H | H | H | H |
| C₃H₇ | H | H | OCH₃ | H | H |
| C₂H₅— | H | —OCH₃ | H | H | H |
| C₂H₅— | H | H | H | —OCH₃ | H |
| C₃H₇ | —OCH₃ | —OCH₃ | H | H | H |
| C₃H₇ | H | —OCH₃ | —OCH₃ | H | H |
| i-C₃H₇— | H | H | H | —OCH₃ | H |
| C₂H₅— | H | H | —OCH₃ | H | —C₆H₅ |

EXAMPLE 5 trans-1a,2,3,4a,5,6-Hexahydro-4-ethyl-9-methoxy-4H-naphth[1,2-b]-1,4-oxazine hydrochloride Step A: Preparation of 7-methoxy-2-oximino-3,4-dihydronaphthalen-1(2H)-one A mixture of potassium tert-butoxide (11.5 gm, 0.1 m), ether (400 ml), tert-butanol (15 ml) and absolute ethanol (15 ml) was refluxed for ½ hour to insure complete solution of the potassium tert-butoxide. To the hot solution was added 7-methoxy-1-tetralone (17.6 gms, 0.1 m) and the reaction mixture turned from yellow to dark brown. To this refluxing solution was added isopentyl nitrite (19 ml). During this addition external heating was not necessary because of the exothermic nature of the reaction. The reaction mixture was refluxed for ½ hour during which time the walls of the flask became coated with a brown solid. After cooling in an ice-bath, the solvent was removed by decantation.

To the solid was added aqueous hydrogen chloride (1 N, 200 ml). After stirring ½ hour, the brown solid was filtered to yield 10 gms (50%) of product.

Step B: Preparation of 2-Acetamido-7-methoxy-3,4-dihydronaphthalen-1(2H)-one A mixture of 2-oximino-7-methoxy-3,4-dihydronaphthalen-1(2H)-one (8.7 gm, 0.04 m), palladium on carbon (10%, 1 gm) tetrahydrofuran (150 ml) and acetic anhydride (25 ml) was hydrogenated on a Parr apparatus for 3 hours. The catalyst was filtered, and the solvents were removed under reduced pressure to yield the product as an oil, which was used in the next step without further purification.

Step C: Preparation of trans-2-Acetamido-7-methoxy-1,2,3,4,-tetrahydronaphthalen-1-ol To a stirred solution of 2-acetamido-7-methoxy-3,4-dihydronaphthalen 1(2H)-one in absolute ethanol (100 ml) was added sodium borohydride (1.6 gms, 0.04 m) in portions. After stirring for ½ hour, acetic acid was added to decompose any excess sodium borohydride. The reaction mixture was poured onto water (150 ml) and this was extracted with ethyl acetate (3×150). The ethyl acetate was washed with aqueous saturated sodium chloride, and was dried over anhydrous sodium sulfate. After filtration, the ethyl acetate was removed under reduced pressure (20 mm) to give a semisolid. The solid was slurried with ether and filtered to yield 3.3 gms (35%) of product as a white solid, m.p. 135°-140° C.

Step D: Preparaton of trans-1a,2,4,4a,5,6-hexahydro-4-ethyl-9-methoxynaphth[1,2-b]-1,4-oxazin-3-one To a suspension of lithium aluminium hydride (2.8 gms, 0.07 m) in tetrahydrofuran (30 ml) at 0°-5° C. was added a slurry of trans-2-acetamido-7-methoxy-1,2,3,4-tetrahydronaphthalen-1-ol (2.16 gms, 0.009 m) in tetrahydrofuran (12 ml) and ethylene glycol diethyl ether (8 ml). During the addition the internal temperature was kept below 10° C. After the addition was completed, the reaction mixture was refluxed for ½ hour. The reaction was cooled to 5°-10° C., and the excess lithium aluminium hydride was hydrolyzed with isopropanol (4.8 ml) and saturated aqueous sodium sulfate (2.4 ml). After the addition of methylene chloride (50 ml), the inorganic salts were removed by filtration through filter cell. The solvent was removed under reduced pressure (20 mm) and the tan solid was disssolved in ethyl acetate (60 ml). To the stirred ethyl acetate solution was added water (90 ml) with sodium carbonate (9 gms) dissolved in it. To the biphasic mixture was added chloroacetyl chloride (1.5 ml) dropwise. The organic layer was separated and was washed with saturated aqueous sodium chloride. After drying over anhydrous sodium sulfate and filtration, the solvent was removed under reduced pressure (20 mm). The oil was dissolved in acetonitrile (7.5 m) and tetrahydrofuran (7.5 ml) and it was added to an ice cold (0°-5° C.) suspension of sodium hydride (0.75 gm, 50%) in tetrahydrofuran (20 ml). The excess sodium hyride was destroyed by addition of absolute ethanol, and the reaction mixture was poured onto water (100 ml). This was extracted with ethyl acetate, and the extract was washed with saturated aqueous sodium chloride. After drying over anhydrous sodium sulfate and filtration, the solvent was removed under reduced pressure (20 mm) to give 1.8 g (77%) of product.

Step E: Preparation of trans-1a,2,3,4a,5,6-hexahydro-4-ethyl-9-methoxy-4H-naphth[1,2-b]-1,4-oxazine hydrochloride To a slurry of lithium aluminium hydride (1.0 gms, 0.02 m) in tetrahydrofuran (20 ml) at 0°-5° C. was added trans-1a,2,4,4a,5,6-hexahydro-4-ethyl-9-methoxynaphth[1,2-b]-1,4-oxazin-3-one (1.8 gms, 0.007 m) in tetrahydrofuran (36 ml) and ethylene glycol dimethyl ether (24 ml). Upon completion of the addition, the reaction mixture was refluxed for ½ hour. After cooling to 0°-5° C., the excess lithium aluminum hydride was hydrolyzed with isopropanol (4.8 ml) and saturated aqueous sodium sulfate (3 ml). After addition of methylene chloride (50 ml), the inorganic salts were collected by filtration through filter cell. The solvents were dried over anhydrous sodium sulfate. After filtration, the organic solvents were removed under reduced pressure (20 mm) to give an oil. The oil was dissolved in ether (50 ml) and ethanolic hydrogen chloride (2.0 ml, 7.2 N) was added. After decantation of the solvent, the solid was recrystallized from methanol to yield 500 mg of product, m.p. 273°-275° C.

Employing the procedure substantially as described in Example 5, Steps A through E, but substituting for the starting material used therein, an equimolecular amount of α-tetralone, 6-methoxy-1-tetralone, 5,6-dimethoxy-1-tetralone, 8-benzyloxy-1-tetralone, 6-benzyloxy-1-tetralone, and 6,7-dimethoxy-1-tetralone, there were produced, respectively:

trans-1a,2,3,4a,5,6-hexahydro-4-ethyl-4H-naphth[1,2-b]-1,4-oxazine hydrochloride, m.p. 218°-221° C. (dec.); and trans-1a,2,3,4a,5,6-hexahydro-4-ethyl-8-methoxy-4H-naphth[1,2-b]-1,4-oxazine hydrochloride, m.p. 210°-213° C.

trans-1a,2,3,4a,5,6-hexahydro-4-ethyl-7,8-dimethoxy-4H-naphth[1,2-b]-1,4-oxazine hydrochloride, m.p. 184°-185° C.

trans-1a,2,3,4a,5,6-hexahydro-10-benzyloxy-4-ethyl-4H-naphth[1,2-b]-1,4-oxazine, (oil);

trans-1a,2,3,4a,5,6-hexahydro-8-benzyloxy-4-ethyl-4H-naphth[1,2-b]-1,4-oxazine, (oil); and trans-1a,2,3,4a,5,6-hexahydro-8,9-dimethoxy-4-ethyl-4H-naphth[1,2-b]-1,4-oxazine hydrochloride, m.p. 287°-289° C. (dec.).

Employing the procedure substantially as described in Example 5, Steps A through E but substituting for the acetic anhydride used in Step B thereof an approximately equimolar amount of propionic anhydride, there was produced in sequence: 2-propionamido-7-methoxy-3,4-dihydro-1(2H)-naphthalenone;

trans-2-propionamido-7-methoxy-1,2,3,4-tetrahydro-1-naphthalenol;

trans-1a,2,3,4a,5,6-hexahydro-9-methoxy-4-propyl-naphth[1,2-b]-1,4-oxazine-3-one; and trans-1a,2,3,4a,5,6-hexahydro-9-methoxy-4-propyl-4H-naphth[1,2-b]-1,4-oxazine hydrochloride, m.p. 237°-241° C.

Similarly, from:
6-benzyloxy-7-methoxy-1-tetralone;
6-methoxy-7-benzyloxy-1-tetralone; and
6,7-dibenzyloxy-1-tetralone
there are produced, respectively, trans-1a,2,3,4a,5,6-hexahydro-8-benzyloxy-9-methoxy-4-propyl-4H-naphth[1,2-b]-1,4-oxazine hydrochloride;

trans-1a,2,3,4a,5,6-hexahydro-8-methoxy-9-benzyloxy-4-propyl-4H-naphth[1,2-b]-1,4-oxazine hydrochloride; and trans-1a,2,3,4a,5,6-hexahydro-8,9-dibenzyloxy-4-propyl-4H-naphth[1,2-b]-1,4-oxazine hydrochloride.

Similarly, using benzoic anhydride there are prepared in sequence:

trans-2-benzamido-7-methoxy-1,2,3,4-tetrahydro-1-naphthalenol;

trans-1a,2,3,4a,5,6-hexahydro-9-methoxy-4-benzyl-naphth[1,2-b]-1,4-oxazine-3-one; and trans-1a,2,3,4a,5,6-hexahydro-9-methoxy-4-benzyl-4H-naphth[1,2-b]-1,4-oxazine hydrochloride.

EXAMPLE 6

(+)- and (−)-trans-1a,2,3,4a,5,6-Hexahydro-4-ethyl-4H-naphth[1,2-b]-1,4-oxazine hydrochloride

Step A: Preparation of 2-Acetamido-3,4-dihydronaphthalen-1(2H)-one

A slurry of 2-oximino-3,4-dihydronaphthalen-[1(2H)-one (8.75 gm, 0.05 m) acetic anhydride (25 ml), tetrahydrofuran (150 ml) and Pd/C (10%, 500 mg) was hydrogenated on a Parr apparatus for 3 hours. The catalyst was removed by filtration through diatomaceous earth. The organic solvents were evaporated under reduced pressure (20 mm) to yield the product as an oil, which was used in the next step without further purification.

Alternatively:

To a stirred biphasic mixture of aqueous sodium bicarbonate (10 gm in 100 ml) and methylene chloride (250 ml) was added 3,4-dihydro-2-aminonaphthalen-1(2H)-one hydrochloride (8.3 gms, 0.04 m). When solution was achieved, acetylchloride (3.9 gms, 0.05 m) was added dropwise. The reacton was stirred for 1 hour. The organic layer was separated, washed with saturated aqueous sodium chloride solution, and dried over anhydrous sodium sulfate. After filtration of the inorganics, the solvent was removed under reduced pressure (20 mm) to give the product as a dark semisolid which was used in the next step without purification.

Step B: Preparation of trans-2-Acetamido-1,2,3,4-tetrahydronaphthalen-1-ol

To a solution of the 2-acetamido-3,4-dihydronaphthalen-1(2H)-one from Step A in absolute ethanol (150 ml) was added sodium borohydride (2.0 gms, 0.05 m) in portions. The reaction mixture was stirred at room temperature for ½ hour. Acetic acid was added dropwise to destroy the excess sodium borohydride. The reaction mixture was poured into water and extracted with ethyl acetate (3×150 ml). The ethyl acetate was washed with saturated aqueous sodium chloride (150 ml) and dried over anhydrous sodium sulfate. After filtration the solvent was removed under reduced pressure to yield 5.5 gms (54%, over Steps A and B), of product as a solid.

Step C: Resolution of trans-2-Acetamido-1,2,3,4-tetrahydronaphthalen-1-ol via 1-α-methoxy mandelic acid esters

Step 1: Ester Formation and Separation

To a stirred mixture of trans 2-acetamido-1,2,3,4-tetrahydronaphthalen-1-ol (1.0 gm, 0.0049 m), N,N′-dicyclohexylcarbodiimide (1.7 gms, 0.0083 m) and 1-α-methoxymandelic acid (1.5 gm, 0.009 m) in methylene chloride (125 ml) was added 4-dimethylaminopyridine (0.2 gm). After filtration of the solid formed, the methylene chloride solution was flash chromatographed to give 450 mg of "top ester" and 400 mg of "bottom ester"; 52% and 45% yield respectively.

Step 2: Saponification to yield (+)-trans-2-acetamido-1,2,3,4-tetrahydronaphthal-en-1-ol and (−)trans-2-acetamido-1,2,3,4-tetrahydronaphthalen-1-ol To a solution of potassium hydroxide (0.52 gm, 0.009 m) in absolute ethanol (20 ml) was added the "top ester" (2.1 gm, 0.005 m) and water (10 drops). The mixture was heated in a hot water bath at 50° C. until solution was achieved (10 mins). The reaction mixture was poured into water, and the solid (160 mg) was filtered. The aqueous layer was extracted with chloroform (3×150 ml). The chloroform was dried over anhydrous sodium sulfate. After filtration, the chloroform was removed under reduced pressure (20 mm) to give a purple solid. The solid was suspended in ether and filtered to yield 0.95 gms (78%) of product as a white solid with a rotation of $[\alpha]_D^{25} = +49.8°$ (C, 0.996 in ethanol).

To a solution of potassium hydroxide (0.39 gm, 0.007 m) in absolute ethanol (20 ml) was added the "bottom ester" (1.6 gm, 0.0045 m) and water (10 drops). The mixture was heated in a hot water bath at 50° C. until solution was achieved (10 mins). The reaction mixture was poured into water and it was extracted with chloroform. The chloroform was dried over anhydrous sodium sulfate. After filtration, the chloroform was removed under reduced pressure (20 mm) to yield B 0.7845 gms (85%) of product as a white solid; $[\alpha]_D^{25} = -41.6°$ (C, 0.0994 in ethanol).

Step D: Preparation of (+)- and (−)-trans-1a,2,-4,4a,5,6-Hexahydro-4-ethylnaphth[1,2-b]-1,4-oxazin-3-one To a suspension of lithium aluminium hydride (0.72 gm, 0.0189 m) in tetrahydrofuran (10 ml) at 0° C. was added a suspension of (+)-trans-2-acetamido-1,2,3,4-tetrahydronaphthalen-1-ol (0.7 gms, 0.0034 m) in tetrahydrofuran (12 ml) and ethylene glycol dimethyl ether (8 ml). During the addition the internal temperature was kept below 10° C. After the addition was completed, the reaction mixture was heated to reflux for ½ hour. After cooling the reaction to 5°–10° C., the excess lithium aluminium hydride was hydrolyzed with isopropanol (1.6 ml) and saturated aqueous sodium sulfate (0.8 ml). After addition of methylene chloride (50 ml), the inorganic salts were removed under reduced pressure, and the oil was dissolved in ethyl acetate (20 ml). To the stirred ethyl acetate solution was added water (20 ml) with sodium carbonate (3.04 g) dissolved in it. To the biphasic mixture was added chloroacetyl chloride (0.48 ml). The organic layer was separated and washed with saturated aqueous sodium chloride. The ethyl acetate was dried over anhydrous sodium sulfate. After filtration, the ethyl acetate was removed under reduced pressure (20 mm) to give an oil. The oil was dissolved in acetonitrile (2.5 ml) and tetrahydrofuran (2.5 ml). This solution was added to a suspension of sodium hydride (0.24 gm, 50%) in tetrahydrofuran (10 ml) at 0°–5° C. After the addition was completed, the excess sodium hydride was destroyed by adding absolute ethanol. The reaction mixture was poured into water and was extracted with ethyl acetate. After the ethyl acetate was washed with saturated aqueous sodium chloride, it was dried over anhydrous sodium sulfate. After filtration, the ethyl acetate was removed under reduced pressure (20 mm) to yield an oil which crystallized to give 550 mg (70% of (+)-product, m.p. 104°–106° C.

The (−)isomer was produced in the same manner using the same reaction conditions to give 450 mg (56%) of (−)-product, m.p. 97°–100° C.

Step E: Preparation of (+)- and (−)-trans-1a,2,3,4a,5,6-hexahydro-4-ethyl-4H-naphth[1,2-b]-1,4-oxazine hydrochloride To a suspension of lithium aluminum hydride (0.5 gm, 0.01 m) in tetrahydrofuran (10 ml) at 0°–5° C. was added (+)-trans-1a,2,4,4a,5,6-hexahydro-4-ethyl-naphth[1,2-b]-1,4-oxazin-3-one (0.55 gm, 0.0024 m) in tetrahydrofuran (12 ml) and ethylene glycol dimethylether (8 ml). Upon completion of the addition, the reaction mixture was refluxed for ½ hour. The reaction mixture was cooled to 0°–5° C. and the excess lithium aluminum hydroxide was hydrolyzed with isopropanol (1.6 ml) and saturated aqueous sodium sulfate (0.8 ml). After addition of methylene chloride (50 ml), the inorganic salts were removed by filtration through filter cell. The solution was dried by anhydrous sodium sulfate. After filtration, the organic solvents were removed under reduced pressure (20 min) to give an oil. The oil was dissolved in ether (100 ml) and ethanolic hydrogen chloride (1.5 ml, 7.2 N) was added. The precipitated solid was recrystallized from methanol to give 149 mg (25%) of (+)-product, m.p. 233°–237° C., $[\alpha]_D^{25} = +56.56°$ (C, 0.944 in ethanol).

(−)-trans-1a,2,3,4a,5,6-Hexahydro-4-ethyl-4H-naphth-[1,2-b]-1,4-oxazine hydrochloride was produced in a similar manner using lithium aluminum hydride (0.35 gm, 0.009 m) and (−)-trans-1a,2,-3,4a,5,6-hexahydro-4-ethylnaphth[1,2-b]-1,4-oxazin-3-one (0.45 gm, 0.002 m) to give 130 mg (26%) of (−)-product; m.p. 230°–234° C., $[\alpha]_D^{25} = -57.10°$ (C, 0.904 in ethanol).

EXAMPLE 7

(+)-trans-1a,2,3,4a,5,6-Hexahydro-9-Methoxy-4-Propyl-4H-Naphth[1,2-b]-1,4-oxazine hydrochloride Step A: Esterification of trans-2-propionamido-7-methoxy-1,2,3,4-tetrahydro-1-naphthalenol with 1-α-methoxymandelic acid and separation of the diastereomeric esters A mixture of equal molar quantities of trans-2-propionamido-7-methoxy-1,2,3,4-tetrahydro-1-naphthalenol, N,N′-dicyclohexylcarbodiimide, and -α-methoxymandelic acid in methylene chloride, containing a catalytic amount of 4-dimethylaminopyridine was stirred at room temperature for 1 hour. The reaction mixture was filtered and subjected to medium pressure chromatography over silica gel. By collecting the proper fractions there were obtained the pure (+) and (−) enantiomeric esters.

Step B: Preparation of (+)-trans-2-propionamido-7-methoxy-1,2,3,4-tetrahydro-1-naphthalenol Material obtained from one of the pure fractions obtained in Step A was dissolved in a solution of potassium hydroxide (slight molar excess) in ethanol and heated at reflux for 10 minutes. The cooled reaction mixture was poured into water, neutralized with dilute hydrochloric acid and the resulting solid was recovered by filtration. Recrystallization from ethyl acetate afforded the subject compound, m.p. 162°–163° C. $[\alpha]_D + 71.02$ (C 0.105 EtOH).

Anal. Calc. for $C_{14}H_{19}NO_3$: C, 67.44; H, 7.68; N, 5.61. Found: C, 67.73; H, 7.93; N, 5.55.

Step C: Preparation of (−)-trans-1a,2,4,4a,5,6-hexahydro-9-methoxy-4-propyl-naphth[1,2-b]-1,4-oxazin-3-one Using essentially the procedure described in Example 6, Step D but employing the product from Step B above as starting material the subject compound was obtained as a solid, 94°–96° C., $[\alpha]_D - 36.94$ (C, 0.0896, EtOH).

Anal. calcd. for $C_{16}H_{21}NO_3$: C, 69.79; H, 7.69; N, 5.09. Found: C, 69.88; H, 8.02, N, 4.96.

Step D: Preparation of (+)-trans-1a,2,3,4a,5,6-hexahydro-9-methoxy-4-propyl-4H-naphth[1,2-b]-1,4-oxazine hydrochloride Using essentially the same procedure as described in Example 6, Step E but employing the product from Step C above as starting material, the subject compound was obtained as a solid m.p. 231°–233° C., $[\alpha]_D + 47.28$ (C 0.105, EtOH).

Anal. Calcd. for $C_{16}H_{23}NO_2 \cdot HCl$: C, 64.52; H, 8.12; N, 4.70. Found: C, 64.24; H, 8.23; N, 4.64.

Employing the procedure substantially as described in Example 7, Steps B, C and D but employing as starting material the other diastereomeric ester obtained in Step A of Example 7, there was obtained in sequence:

(−)-trans-2-propionamido-7-methoxy 1,2,3,4-tetrahydro-1-naphthalenol;

(+)-trans-1a,2,3,4a,5,6-hexahydro-9-methoxy-4-propyl-naphth[1,2-b]-1,4-oxazin-3-one; and (−)-trans-1a,2,3,4a,5,6-hexahydro-9-methoxy-4-propyl-4H-naphth[1,2-b]-1,4-oxazine hydrochloride, m.p. 231°–233° C., $[\alpha] -47.44$ (0.0978, EtOH).

Anal. Calcd. for $C_{16}H_{23}NO_2 \cdot HCl$: C, 64.52; H, 8.12; N, 4.70. Found: C, 64.68; H, 8.37; N, 4.66.

EXAMPLE 8

(+)-trans-1a,2,3,4a,5,6-hexahydro-9-methoxy-4-ethyl-4H-Naphth[1,2-b]-1,4-oxazine hydrochloride Employing the procedures substantially as described in Example 7, Step A, but substituting for the propionamido compound used therein, an equimolar amount of the acetamido homolog, there was obtained the separated, pure diastereomeric esters.

Taking one of the foregoing esters through the procedures as described in Example 7, Steps B, C and D there were produced in sequence:

(+)-trans-2-acetamido-7-methoxy-1,2,3,4-tetrahydro-1-naphthalenol;

trans-1a,2,3,4a,5,6-hexahydro-9-methoxy-4-ethyl-naphth[1,2-b]-1,4-oxazin-3-one; and (+)-trans-1a,2,3,4a,5,6-hexahydro-9-methoxy-4-ethyl-4H-naphth[1,2-b]-1,4-oxazine hydrochloride, m.p. 286°-288° C. (dec.).

Anal. Calcd. for $C_{15}H_{21}NO_2HCl$: C, 63.48; H, 7.82; N, 4.94. Found: C, 63.08; H, 8.05; N, 5.01.

From the other diastereomeric ester of Example 8, using the procedures described in Example 7, Steps B, C and D, there were obtained in sequence:

(−)-trans-2-acetamido-7-methoxy-1,2,3,4-tetrahydro-1-naphthalenol;

(−)-trans-1a,2,3,4a,5,6-hexahydro-9-methoxy-4-ethyl-naphth[1,2-b]-1,4-oxazin-3-one; and (−)-trans-1a,2,3,4a,5,6-hexahydro-9-methoxy-4-ethyl-4H-naphth[1,2-b]-1,4-oxazine hydrochloride, 282°-283° C. (dec.).

Anal. Calcd. for $C_{15}H_{21}NO_2 \cdot HCl$: C, 63.48; H, 7.82; N, 4.94. Found: C, 63.22; H, 8.06; N, 4.91.

Employing the procedures used in Example 6, 7 and 8, the other novel trans compounds of this invention are produced as optically pure products, such as (+) and (−)-trans-1a,2,3,4a,5,6-hexahydro-9-methoxy-4-benzyl-4H-naphth[1,2-b]-1,4-oxazine hydrochloride.

EXAMPLE 9 trans-1a,2,3,4a,5,6-hexahydro-7-hydroxy-4-ethyl-4H-naphth[1,2-b]-1,4-oxazine hydrochloride An intimate mixture of pyridine hydrochloride (312 mg, 0.27 mmole) and trans-1a,2,3,4a,5,6-hexahydro-4-ethyl-7-methoxy-4H-naphth[1,2-b]-1,4-oxazine hydrochloride (250 mg, 0.09 mmole) was heated at 200° C. for 5 hours. The cooled reaction mixture was made slightly basic with NH4OH and then extracted with chloroform (3×50 ml). The organic phase was washed with brine, dried over MgSO4, and then concentrated to dryness in vacuo. The resulting solid was dissolved in ethyl acetate and some 4 N ethanolic hydrochloric acid was added which caused the precipitation of the product. The yield was 60 mg (25%), m.p. 294°-297° C. (dec.) (isopropanol).

Similarly, but omitting the treatment with ethanolic hydrogen chloride, there were prepared from the corresponding methoxy compounds:

trans-1a,2,3,4a,5,6-hexahydro-4-ethyl-9-hydroxy-4H-naphth[1,2-b]-1,4-oxazine, m.p. 223°-225° C.;

trans-1a,2,3,4a,5,6-hexahydro-4-propyl-9-hydroxy-4H-naphth[1,2-b]-1,4-oxazine, m.p. 164°-166° C.;

(+)-trans-1a,2,3,4a,5,6-hexahydro-4-ethyl-9-hydroxy-4H-naphth[1,2-b]-1,4-oxazine, m.p. 165°-168° C., $[\alpha]_D+51.77$, (C, 0.101, EtOH);

(−)-trans-1a,2,3,4a,5,6-hexahydro-4-ethyl-9-hydroxy-4H-naphth[1,2-b]-1,4-oxazine, m.p. 164°-166° C., $[\alpha]_D-45.45$, (C, 0.101, EtOH);

(+)-trans-1a,2,3,4a,5,6-hexahydro-9-hydroxy-4-propyl-4H-naphth[1,2-b]-1,4-oxazine, m.p. 158°-160° C., $[\alpha]_D+59.54$, (C, 0.0964, EtOH); and (−)-trans-1a,2,3,4a,5,6-hexahydro-9-hydroxy-4-propyl-4H-naphth[1,2-b]-1,4-oxazine, m.p. 158°-161° C., $[\alpha]_D-62.63$, (C, 0.0942, EtOH).

Employing the procedure substantially as described in Example 9, but substituting for the trans-1a,2,3,4a,5,6-hexahydro-4-ethyl-7-methoxy-4H-nahth[1,2-b]-1,4-oxazine hydrochloride used as starting material therein, an equimolar amount of the alkoxynaphthoxaznes describe in Table IV, there are produced the corresponding hydroxynaphthoxazines, also described in Table IV in accordance with the following reaction:

TABLE IV

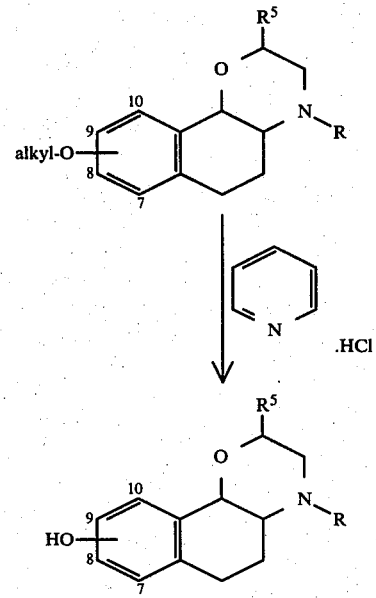

| | STARTING MATERIALS | | | | PRODUCTS | | | | |
|---|---|---|---|---|---|---|---|---|---|
| R | 7 | 8 | 9 | 10 | 7 | 8 | 9 | 10 | $R^5$ |
| $CH_2=CHCH_2-$ | $-OCH_3$ | H | H | H | $-OH$ | H | H | H | H |
| $CH_3-$ | $-OCH_3$ | H | H | H | $-OH$ | H | H | H | H |
| $C_6H_5CH_2-$ | $-OCH_3$ | H | H | H | $-OH$ | H | H | H | H |
| $C_3H_7-$ | $-OCH_3$ | H | H | H | $-OH$ | H | H | H | H |
| $C_3H_7-$ | H | H | $-OCH_3$ | H | H | H | $-OH$ | H | $-CH_3$ |
| $C_2H_5-$ | H | H | $-OCH_3$ | H | H | H | $-OH$ | H | $-C_6H_5$ |
| $i-C_3H_7-$ | H | H | H | $-OCH_3$ | H | H | H | $-OH$ | H |
| H | H | H | $-OCH_3$ | H | H | H | $-OH$ | H | H |

TABLE IV-continued

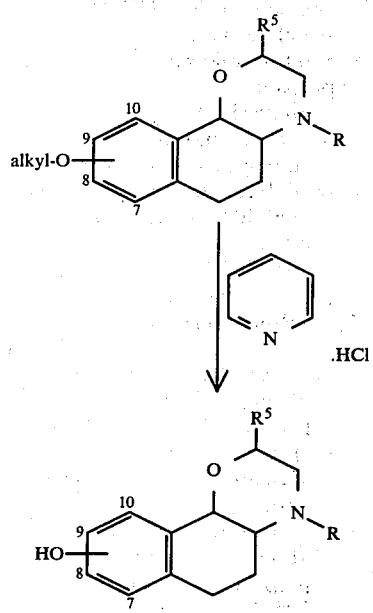

| R | STARTING MATERIALS | | | | PRODUCTS | | | | |
|---|---|---|---|---|---|---|---|---|---|
| | 7 | 8 | 9 | 10 | 7 | 8 | 9 | 10 | $R^5$ |
| H | H | H | H | —OCH$_3$ | H | H | H | —OH | H |
| H | —OCH$_3$ | H | H | H | —OH | H | H | H | H |
| H | H | H | —OC$_3$H$_7$ | H | H | H | —OH | H | H |
| H | —OC$_2$H$_5$ | H | H | H | —OH | H | H | H | H |

EXAMPLE 10 trans-1a,2,3,4a,5,6-hexahydro-10-hydroxy-4-ethyl-4H-naphth[1,2-b]-1,4-oxazine hydrochloride The 10-benzyloxy material from Example 5 was dissolved in C$_2$H$_5$OH:THF (1:1 v/v), 10% palladium on carbon catalyst was added and the reaction mixture was hydrogenated on a Parr apparatus at 25 psi until hydrogen uptake ceased. The reaction mixture was removed from the Parr, filtered, and the solvent was removed in vacuo. The residue was purified by medium pressure chromatography using CHCl$_3$.CH$_3$OH (9:1 v/v) to elute. The subject compound was obtained as a white solid (hydrogen chloride gas added to an ethanol solution).

Employing the procedure substantially as described in Example 10, but starting with the 8-benzyloxy compound, also from Example 5, there was produced trans-1a,2,3,4a,5,6-hexahydro-8-hydroxy-4-ethyl-4H-naphth[1,2-b]-1,4-oxazine, m.p. 187°–191° C.

Employing the procedure substantially as described in Example 10 but starting with trans-1a,2,3,4a,5,6-hexahydro-8-benzyloxy-9-methoxy-4-propyl-4H-naphth[1,2-b]-1,4-oxazine hydrochloride;

trans-1a,2,3,4a,5,6-hexahydro-8-methoxy-9-benzyloxy-4-propyl-4H-naphth[1,2-b]-1,4-oxazine hydrochloride; and trans-1a,2,3,4a,5,6-hexahydro-8,9-dibenzyloxy-4-propyl-4H-naphth[1,2-b]-1,4-oxazine hydrochloride;

there are produced respectively:

trans-1a,2,3,4a,5,6-hexahydro-8-hydroxy-9-methoxy-4-propyl-4H-naphth[1,2-b]-1,4-oxazine hydrochloride;

trans-1a,2,3,4a,5,6-hexahydro-8-methoxy-9-hydroxy-4-propyl-4H-naphth[1,2-b]-1,4-oxazine hydrochloride; and trans-1a,2,3,4a,5,6-hexahydro-8,9-dihydroxy-4-propyl-4H-naphth[1,2-b]-1,4-oxazine hydrochloride.

Employing the procedure substantially as described in Example 10 but starting with the (+) or (−)-trans-1a,2,3,4a,5,6-hexahydro-9-methoxy-4-benzyl-4H-naphth[1,2-b]-1,4-oxazine from Example 8 there are produced:

(+)-trans-1a,2,3,4a,5,6-hexahydro-9-methoxy-4H-naphth[1,2-b]-1,4-oxazine hydrochloride; and (−)-trans-1a,2,3,4a,5,6-hexahydro-9-methoxy-4H-naphth[1,2-b]-1,4-oxazine hydrochloride, respectively.

EXAMPLE 11 trans-1a,2,3,4a,5,6-hexahydro 9-acetoxy-4-propyl-4H-naphth[1,2-b]-1,4-oxazine hydrochloride A mixture of trans-1a,2,3,4a,5,6-hexahydro 9-hydroxy-4-propyl-4H-naphth[1,2-b]-1,4-oxazine (0.7 g., 2.8 mmole), acetic anhydride (6 ml) and 4-dimethylaminopyridine (10 mg) was stirred and heated at 85°–90° C. for 1 hour. Most of the solvent was removed in vacuo and the residue was taken up in ethyl acetate (25 ml). Addition of ethanolic hydrogen chloride afforded the subject compound in 54% yield, m.p. 218°–220° (CH$_3$CN).

Anal. calcd. for C$_{17}$H$_{23}$NO$_3$.HCl: C, 62.66; H, 7.42; N, 4.30. Found: C, 62.25; H, 7.56; N, 4.40.

EXAMPLE 12 trans-1a,2,3,4a,5,6-hexahydro-9-pivaloyloxy-4-propyl-4H-naphth[1,2-b]-1,4-oxazine hydrochloride This compound was prepared by essentially the same procedure described in Example 11 by substituting trimethylacetic anhydride for the acetic anhydride used in that example. The yield was 80%; m.p. 248°–250°.

Anal. Calcd. for $C_{20}H_{29}NO_3 \cdot HCl$ C, 65.29; H, 8.22; N, 3.81. Found: C, 65.18; H, 8.57; N, 3.66.

EXAMPLE 13 trans-1a,2,3,4a,5,6-hexahydro-9-dimethyl-carbamyloxy-4-propyl-4H-naphth[1,2-b]-1,4-oxazine To a cooled (5°–10°) solution of trans-1a,2,3,4a,5,6-hexahydro-9-hydroxy-4-pyropyl-4H-naphth[1,2-b]-1,4-oxazine (1.0 g, 0.04 m) in dry pyridine (10 ml) was added a pyridine (5 ml) solution of dimethylcarbamyl chloride (0.5 g, 0.04 m). The reaction mixture was stirred for 2 hr. and then placed in the refrigerator overnight. The reaction mixture was poured on ice, the resulting solid was recovered by filtration and recrystallized to afford the subject compound.

Employing the procedures substantially as described in Examples 11, 12 and 13 but substituting for the acid anhydrides, carbamyl chloride and the hydroxy-naphthoxazines used therein, comparable amounts of the anhydride of formula $(R^7CO)_2O$ or carbamyl chloride of formula $R^7COCl$ and the hydroxy-naphthaoxazines identified in Table V, there are produced the acyloxynaphthoxazines also described in Table V, in accordance with the following reaction scheme:

TABLE V
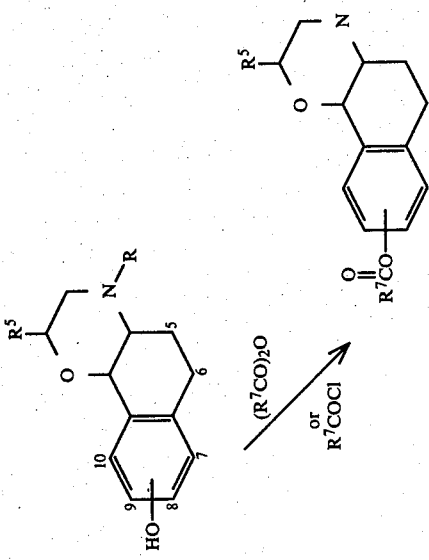
| | | STARTING COMPOUND | | | | | FINAL PRODUCT | | | |
|---|---|---|---|---|---|---|---|---|---|---|
| Isomer | R | 7 | 8 | 9 | 10 | 7 | 8 | 9 | 10 | $R^5$ |
| (±)-trans | —$C_2H_5$ | H | H | —OH | H | H | H | —OCCH$_3$ (O=) | H | H |
| (+)-trans | —$C_2H_5$ | H | H | —OH | H | H | H | —OCCH$_3$ (O=) | H | H |
| (−)-trans | —$C_2H_5$ | H | H | —OH | H | H | H | —OCCH$_3$ (O=) | H | H |
| (+)-trans | —$C_3H_7$ | H | H | —OH | H | H | H | —OCCH$_3$ (O=) | H | H |
| (−)-trans | —$C_3H_7$ | H | H | —OH | H | H | H | —OC—CH$_3$ (O=) | H | H |
| (±)-trans | —$C_2H_5$ | H | H | —OH | H | H | H | —OC—CH$_3$ (O=) | H | H |
| (+)-trans | —$C_2H_5$ | H | H | —OH | H | H | H | —OCC(CH$_3$)$_3$ (O=) | H | H |
| | | | | | | | | —OCC(CH$_3$)$_3$ (O=) | | |

TABLE V-continued

| Isomer | R | STARTING COMPOUND | | | | | FINAL PRODUCT | | | | |
|---|---|---|---|---|---|---|---|---|---|---|---|
| | | 7 | 8 | 9 | 10 | 7 | 8 | 9 | 10 | R$^5$ |
| (−)-trans | —C$_2$H$_5$ | H | H | —OH | H | H | H | —OC(=O)C(CH$_3$)$_3$ | H | H |
| (+)-trans | —C$_3$H$_7$ | H | H | —OH | H | H | H | —OC(=O)C(CH$_3$)$_3$ | H | H |
| (−)-trans | —C$_3$H$_7$ | H | H | —OH | H | H | H | —OC(=O)C(CH$_3$)$_3$ | H | H |
| (±)-trans | —C$_2$H$_5$ | H | H | —OH | H | H | H | —OC(=O)CH$_2$C$_6$H$_5$ | H | H |
| (+)-trans | —C$_2$H$_5$ | H | H | —OH | H | H | H | —OC(=O)CH$_2$C$_6$H$_5$ | H | H |
| (−)-trans | —C$_2$H$_5$ | H | H | —OH | H | H | H | —OC(=O)CH$_2$C$_6$H$_5$ | H | H |
| (±)-trans | —C$_3$H$_7$ | H | H | —OH | H | H | H | —OC(=O)CH$_2$C$_6$H$_5$ | H | H |

TABLE V-continued
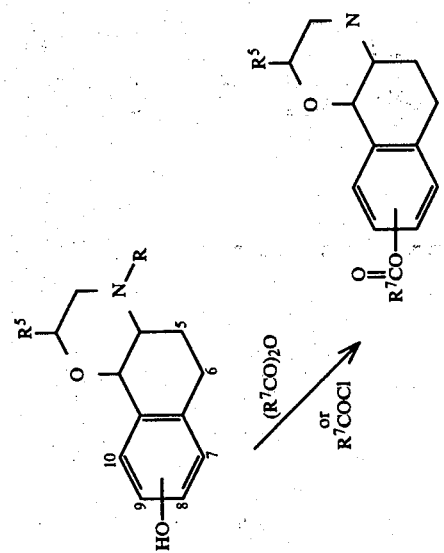
| Isomer | R | STARTING COMPOUND | | | | FINAL PRODUCT | | | | |
|---|---|---|---|---|---|---|---|---|---|---|
| | | 7 | 8 | 9 | 10 | 7 | 8 | 9 | 10 | $R^5$ |
| (+)-trans | —$C_3H_7$ | H | H | —OH | H | H | H | —OCCH$_2$C$_6$H$_5$ (C=O) | H | H |
| (−)-trans | —$C_3H_7$ | H | H | —OH | H | H | H | —OCCH$_2$C$_6$H$_5$ (C=O) | H | H |
| (±)-trans | —$C_2H_5$ | —OH | H | H | H | —OCCH$_3$ (C=O) | H | H | H | H |
| (±)-trans | —$C_2H_5$ | H | H | H | —OH | —OH | H | H | H | H |
| (±)-trans | —$C_2H_5$ | H | —OH | H | H | H | —OCC$_6$H$_5$ (C=O) | H | H | H |
| (±)-trans | —CH$_2$CH=CH$_2$ | —OH | H | H | H | —OCC$_6$H$_{11}$ (C=O) | H | H | H | H |

TABLE V-continued

Starting compound structure:

Structure showing tetrahydronaphthalene with 7-OH, positions 5,6,7,8,9,10 labeled, with -O-CH(R⁵)-CH₂-NHR side chain $(R^7CO)_2O$ or $R^7COCl$ →

Final product: same tetrahydronaphthalene skeleton with R⁷CO-O- at position 7, and side chain -O-CH(R⁵)-CH₂-N(R)(R⁷CO-)

| Isomer | R | STARTING COMPOUND | | | | FINAL PRODUCT | | | | | |
|---|---|---|---|---|---|---|---|---|---|---|---|
| | | 7 | 8 | 9 | 10 | 7 | 8 | 9 | 10 | R⁵ |
| (±)-trans | —CH₃ | —OH | H | H | H | 4-Cl, 3-Cl-C₆H₃-C(=O)-O— | H | H | H | H |
| (±)-trans | —CH₂C₆H₅ | —OH | H | H | H | 4-OCH₃, 3-OCH₃-C₆H₃-C(=O)-O— | H | H | H | H |
| (±)-trans | —C₃H₇ | —OH | H | H | H | 4-CH₃, 3-CH₃-C₆H₃-C(=O)-O— | H | H | H | H |
| (±)-trans | —C₃H₇—i | H | H | H | —OH | H | H | H | H | —OCCH₂ (with =O) |

TABLE V-continued
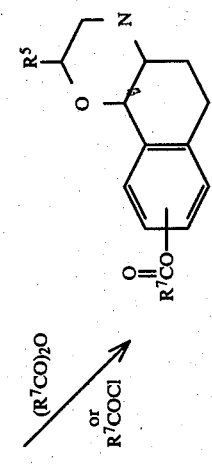
| | STARTING COMPOUND | | | | | FINAL PRODUCT | | | |
|---|---|---|---|---|---|---|---|---|---|
| Isomer | R | 7 | 8 | 9 | 10 | 7 | 8 | 9 | 10 | R⁵ |
| (±)-trans | H | H | H | —OH | H | H | H | —OC(=O)CH₂-(2,3-diOCH₃-C₆H₃) | H | H |
| (±)-trans | H | H | H | H | H | H | H | H | —OC(=O)CH₂-(2,3-diCH₃-C₆H₃) | H |
| (±)-trans | —C₃H₇ | H | H | —OH | H | H | H | —OC(=O)CH₃ | H | —CH₃ |
| (±)-trans | —C₂H₅ | H | H | —OH | H | H | H | —OC(=O)CH₃ | H | —C₆H₅ |
| (±)-trans | —C₂H₅ | H | H | —OH | H | H | H | —OC(=O)N(CH₃)₂ | H | H |

TABLE V-continued
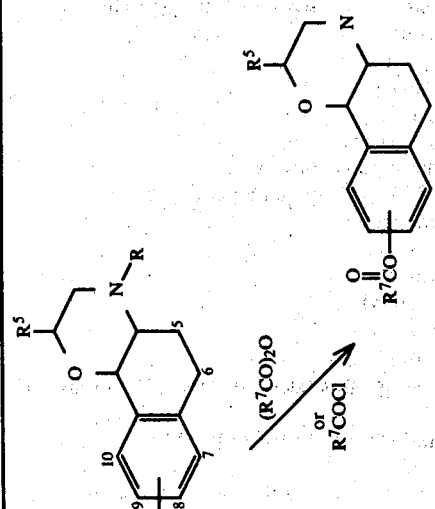
| Isomer | R | STARTING COMPOUND | | | | FINAL PRODUCT | | | | |
|---|---|---|---|---|---|---|---|---|---|---|
| | | 7 | 8 | 9 | 10 | 7 | 8 | 9 | 10 | $R^5$ |
| (±)-trans | $-C_2H_7$ | H | H | $-OH$ | H | H | H | $-OCN$ piperidine(C=O) | H | H |
| (±)-trans | $-C_2H_7$ | H | H | $-OH$ | H | H | H | $-OC$ morpholine(C=O) | H | H |
| (±)-trans | $-C_2H_7$ | H | H | $-OH$ | H | H | H | $-OC$ piperazine-NH | H | H |
| (±)-trans | $-C_2H_7$ | H | H | $-OH$ | H | H | H | $-OC$ piperazine-N-$CH_3$ | H | H |
| (±)-trans | $-C_2H_7$ | H | H | $-OH$ | H | H | H | $-O-C-NHCH_3$ | H | H |

EXAMPLE 14

Pharmaceutical Composition

A typical tablet containing 100 mg of active ingredient per tablet is prepared by mixing together with the active ingredient, calcium phosphate, lactose and starch in the amounts shown in the table below. After these ingredients are thoroughly mixed, the appropriate amount of magnesium stearate is added and the dry mixture blended for an additional three minutes. This mixture is then compressed into tablets.

| Tablet Formula | |
| --- | --- |
| Ingredient | Mg. per Tablet |
| Trans-1a,2,3,4a,5,6-hexahydro-9-hydroxy-4-propyl-4H—naphth-[1,2-b]-1,4-oxazine hydrochloride | 100 mg |
| Calcium phosphate | 52 mg |
| Lactose | 60 mg |
| Starch | 10 mg |
| Magnesium Stearate | 1 mg |

Similarly prepared are tablets comprising as active ingredient any of the other novel compounds described herein.

What is claimed is:

1. A compound of structural formula:

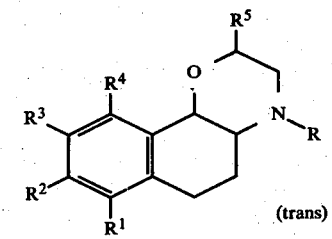

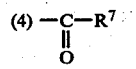

with positive, negative or zero optical activity, wherein:
R is
 (a) hydrogen,
 (b) $C_{1-4}$ alkyl,
 (c) $C_{2-5}$ alkenyl,
 (d) phenyl-$C_{1-4}$ alkyl; and
$R^1$, $R^2$, $R^3$ and $R^4$ are independently:
 (a) hydrogen,
 (b) $C_{1-4}$ alkyl,
 (c) halo,
 (d) $OR^6$ wherein $R^6$ is
  (1) hydrogen
  (2) $C_{1-3}$ alkyl,
  (3) phenyl-$C_{1-3}$alkyl,
  (4) $-\underset{\underset{O}{\parallel}}{C}-R^7$ wherein $R^7$ is
  (i) $C_{1-6}$ alkyl
  (ii) $C_{3-6}$ cycloalkyl,
  (iii) phenyl-$C_{1-3}$ alkyl, wherein the phenyl group is unsubstituted or substituted with one or more of halo, $C_{1-3}$ alkyl or $C_{1-3}$ alkoxy,
  (iv) pyridyl-$C_{1-3}$ alkyl,
  (v) furyl-$C_{1-3}$ alkyl,
  (vi) phenyl, either unsubstituted or substituted with one or more of halo, $C_{1-3}$ alkyl or $C_{1-3}$ alkoxy,
  (vii) pyridyl,
  (viii) furyl,
  (ix) $-NR^8R^9$ wherein $R^8$ and $R^9$ are independently hydrogen or $C_{1-3}$ alkyl, or $R^8$ and $R^9$ are joined together to form a heterocycle selected from piperidinyl, morpholinyl, piperazinyl and N-$C_{1-3}$ alkylpiperazinyl; and
$R^5$ is hydrogen, $C_{1-3}$ alkyl or phenyl.

2. The compound of claim 1 of structural formula:

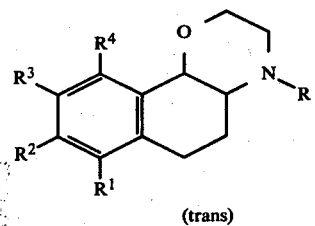

with positive, negative or zero optical activity, or a pharmaceutically acceptable salt thereof, wherein:
R is
 (a) hydrogen,
 (b) $C_{1-4}$ alkyl,
 (c) $C_{2-5}$ alkenyl, or
 (d) phenyl-$C_{1-4}$ alkyl; and
$R^1$, $R^2$, $R^3$ and $R^4$ are independently:
 (a) hydrogen,
 (b) $C_{1-3}$ alkoxy,
 (c) hydroxy,
 (d) $C_{1-4}$alkyl,
 (e) halo,
 (f) phenyl-$C_{1-3}$alkoxy, or
 (g) adjacent R groups taken together are methylenedioxy.

3. The compound of claim 2 with zero optical activity.

4. The compound of claim 2 with positive optical activity.

5. The compound of claim 2 with negative optical activity.

6. The compound of claims 1, 2, 3, 4, or 5 wherein R is $C_{1-4}$ alkyl and one or more of $R^1$, $R^2$, $R^3$ and $R^4$ is hydroxy, or alkoxy.

7. The compound of claims 1, 2, 3, 4 or 5 wherein R is n-propyl, $R^3$ is hydroxy or methoxy and $R^1$, $R^2$ and $R^4$ are hydrogen.

8. A pharmaceutical formulation for the treatment of Parkinsonism or hypertension comprising a pharmaceutical carrier and an effective amount of a compound of structural formula:

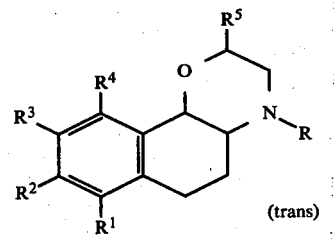

with positive or zero optical activity, or a pharmaceutically acceptable salt thereof, wherein:

R is
(a) hydrogen,
(b) $C_{1-4}$ alkyl,
(c) $C_{2-5}$ alkenyl,
(d) phenyl-$C_{1-4}$ alkyl; and $R^1$, $R^2$, $R^3$ and $R^4$ are independently:
(a) hydrogen,
(b) $C_{1-4}$ alkyl,
(c) halo,
(d) $OR^6$ wherein $R^6$ is
  (1) hydrogen
  (2) $C_{1-3}$ alkyl,
  (3) phenyl-$C_{1-3}$alkyl,

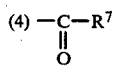

wherein $R^7$ is
(i) $C_{1-6}$ alkyl
(ii) $C_{3-6}$ cycloalkyl,
(iii) phenyl-$C_{1-3}$ alkyl, wherein the phenyl group is unsubstituted or substituted with one or more of halo, $C_{1-3}$ alkyl or $C_{1-3}$ alkoxy,
(iv) pyridyl-$C_{1-3}$ alkyl,
(v) furyl-$C_{1-3}$ alkyl,
(vi) phenyl, either unsubstituted or substituted with one or more of halo, $C_{1-3}$ alkyl or $C_{1-3}$ alkoxy,
(vii) pyridyl,
(viii) furyl,
(ix) $-NR^8R^9$ wherein $R^8$ and $R^9$ are independently hydrogen or $C_{1-3}$ alkyl, or $R^8$ and $R^9$ are joined together to form a heterocycle selected from piperidinyl, morpholinyl, piperazinyl and N-$C_{1-3}$ alkylpiperazinyl; and $R^5$ is hydrogen, $C_{1-3}$ alkyl or phenyl.

9. The pharmaceutical formulation of claim 8 for the treatment of Parkinsonism or hypertension comprising a pharmaceutical carrier and an effective amount of a compound of structural formula:

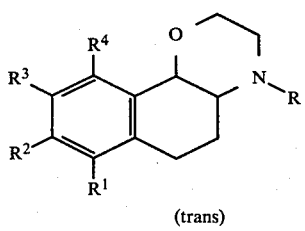

(trans)

with positive or zero optical activity, or a pharmaceutically acceptable salt thereof, wherein:

R is
(a) hydrogen,
(b) $C_{1-4}$ alkyl,
(c) $C_{2-5}$ alkenyl, or
(d) phenyl-$C_{1-4}$ alkyl; and $R^1$, $R^2$, $R^3$ and $R^4$ are independently:
(a) hydrogen,
(b) $C_{1-3}$ alkoxy,
(c) hydroxy,
(d) $C_{1-4}$alkyl,
(e) halo,
(f) phenyl-$C_{1-3}$alkoxy, or
(g) adjacent R groups taken together are methylenedioxy;

10. The formulation of claim 9 wherein the compound has positive optical activity.

11. The formulation of claims 8, 9 or 10 wherein R is $C_{1-4}$ alkyl and one or more of $R^1$, $R^2$, $R^3$ and $R^4$ is hydroxy, or methoxy.

12. The formulation of claims 8, 9 or 10 wherein R is n-propyl, $R^3$ is hydroxy or methoxy and $R^1$, $R^2$ and $R^4$ are hydrogen.

13. A pharmaceutical formulation for the treatment of Parkinsonism comprising a pharmaceutical carrier, an effective amount of an art-recognized antiparkinsonism agent, and an effective amount of a compound of structural formula:

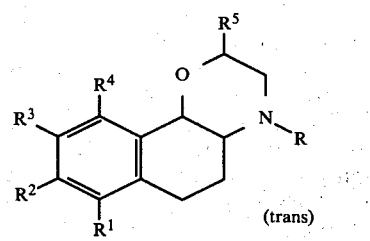

(trans)

with positive or zero optical activity, or a pharmaceutically acceptable salt thereof, wherein:

R is
(a) hydrogen,
(b) $C_{1-4}$ alkyl,
(c) $C_{2-5}$ alkenyl,
(d) phenyl-$C_{1-4}$ alkyl; and $R^1$, $R^2$, $R^3$ and $R^4$ are independently:
(a) hydrogen,
(b) $C_{1-4}$ alkyl,
(c) halo,
(d) $OR^6$ wherein $R^6$ is
  (1) hydrogen
  (2) $C_{1-3}$ alkyl,
  (3) phenyl-$C_{1-3}$alkyl,

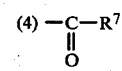

wherein $R^7$ is
(i) $C_{1-6}$ alkyl
(ii) $C_{3-6}$ cycloalkyl,
(iii) phenyl-$C_{1-3}$ alkyl, wherein the phenyl group is unsubstituted or substituted with one or more of halo, $C_{1-3}$ alkyl or $C_{1-3}$ alkoxy,
(iv) pyridyl-$C_{1-3}$ alkyl,
(v) furyl-$C_{1-3}$ alkyl,
(vi) phenyl, either unsubstituted or substituted with one or more of halo, $C_{1-3}$ alkyl or $C_{1-3}$ alkoxy,
(vii) pyridyl,
(viii) furyl,
(ix) $-NR^8R^9$ wherein $R^8$ and $R^9$ are independently hydrogen or $C_{1-3}$ alkyl, or $R^8$ and $R^9$ are joined together to form a heterocycle selected from piperidinyl, morpholinyl, piperazinyl and N-$C_{1-3}$ alkylpiperazinyl; and $R^5$ is hydrogen, $C_{1-3}$ alkyl or phenyl.

14. The pharmaceutical formulation of claim 13 for the treatment of Parkinsonism comprising a pharmaceutical carrier, an effective amount of an art-recognized antiparkinsonism agent, and an effective amount of a compound of structural formula:

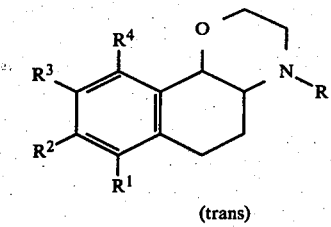

(trans)

with positive or zero optical activity, or a pharmaceutically acceptable salt thereof, wherein:

R is
  (a) hydrogen,
  (b) $C_{1-4}$ alkyl,
  (c) $C_{2-5}$ alkenyl, or
  (d) phenyl-$C_{1-4}$ alkyl; and
$R^1$, $R^2$, $R^3$ and $R^4$ are independently:
  (a) hydrogen,
  (b) $C_{1-3}$ alkoxy,
  (c) hydroxy,
  (d) $C_{1-4}$alkyl,
  (e) halo,
  (f) phenyl-$C_{1-3}$alkoxy, or
  (g) adjacent R groups taken together are methylenedioxy;

15. The formulation of claim 14 wherein the compound has positive optical activity.

16. The formulation of claims 13, 14 or 15 wherein R is $C_{1-4}$ alkyl and one or more of $R^1$, $R^2$, $R^3$ and $R^4$ is hydroxy, or methoxy.

17. The formulation of claims 13, 14 or 15 wherein R is n-propyl, $R^3$ is hydroxy or methoxy and $R^1$, $R^2$ and $R^4$ are hydrogen.

18. A method of treating Parkinsonism or hypertension which comprises the administration to a patient in need of such treatment of an effective amount of a compound of structural formula:

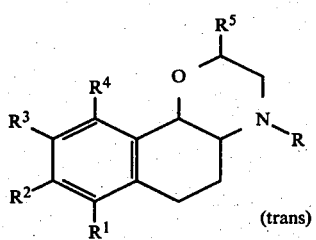

(trans)

with positive or zero optical activity, or a pharmaceutically acceptable salt thereof, wherein:

R is
  (a) hydrogen,
  (b) $C_{1-4}$ alkyl,
  (c) $C_{2-5}$ alkenyl,
  (d) phenyl-$C_{1-4}$ alkyl; and
$R^1$, $R^2$, $R^3$ and $R^4$ are independently:
  (a) hydrogen,
  (b) $C_{1-4}$ alkyl,
  (c) halo,
  (d) $OR^6$ wherein $R^6$ is
    (1) hydrogen
    (2) $C_{1-3}$ alkyl,
    (3) phenyl-$C_{1-3}$alkyl,

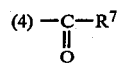

wherein $R^7$ is
    (i) $C_{1-6}$ alkyl
    (ii) $C_{3-6}$ cycloalkyl,
    (iii) phenyl-$C_{1-3}$ alkyl, wherein the phenyl group is unsubstituted or substituted with one or more of halo, $C_{1-3}$ alkyl or $C_{1-3}$ alkoxy,
    (iv) pyridyl-$C_{1-3}$ alkyl,
    (v) furyl-$C_{1-3}$ alkyl,
    (vi) phenyl, either unsubstituted or substituted with one or more of halo, $C_{1-3}$ alkyl or $C_{1-3}$ alkoxy,
    (vii) pyridyl,
    (viii) furyl,
    (ix) $-NR^8R^9$ wherein $R^8$ and $R^9$ are independently hydrogen or $C_{1-3}$ alkyl, or $R^8$ and $R^9$ are joined together to form a heterocycle selected from piperidinyl, morpholinyl, piperazinyl and N-$C_{1-3}$ alkylpiperazinyl; and
  $R^5$ is hydrogen, $C_{1-3}$ alkyl or phenyl.

19. The method of claim 18 for treating Parkinsonism or hypertension which comprises the administration to a patient in need of such treatment of an effective amount of a compound of structural formula:

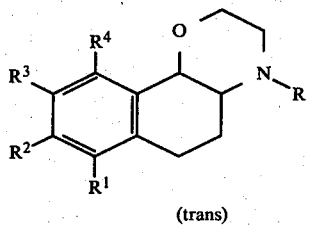

(trans)

with positive or zero optical activity, or a pharmaceutically acceptable salt thereof, wherein:

R is
  (a) hydrogen,
  (b) $C_{1-4}$ alkyl,
  (c) $C_{2-5}$ alkenyl, or
  (d) phenyl-$C_{1-4}$ alkyl; and
$R^1$, $R^2$, $R^3$ and $R^4$ are independently:
  (a) hydrogen,
  (b) $C_{1-3}$ alkoxy,
  (c) hydroxy,
  (d) $C_{1-4}$alkyl,
  (e) halo,
  (f) phenyl-$C_{1-3}$alkoxy, or
  (g) adjacent R groups taken together are methylenedioxy.

20. The method of claim 19 wherein the compound has positive optical activity.

21. The method of claims 18, 19 or 20 wherein R is $C_{1-4}$ alkyl and one or more of $R^1$, $R^2$, $R^3$ and $R^4$ is hydroxy or methoxy.

22. The method of claim 18, 19 or 20, wherein R is n-propyl, $R^3$ is hydroxy or methoxy and $R^1$, $R^2$ and $R^4$ are hydrogen.

23. A method of treating Parkinsonism which comprises the administration to a patient in need of such treatment of an effective amount of an art-recognized antiparkinsonism agent and of an effective amount of a compound of structural formula:

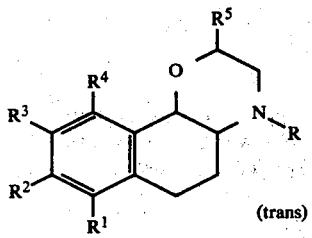
(trans)

with positive or zero optical activity, or a pharmaceutically acceptable salt thereof, wherein:

R is
 (a) hydrogen,
 (b) $C_{1-4}$ alkyl,
 (c) $C_{2-5}$ alkenyl,
 (d) phenyl-$C_{1-4}$ alkyl; and
$R^1$, $R^2$, $R^3$ and $R^4$ are independently:
 (a) hydrogen,
 (b) $C_{1-4}$ alkyl,
 (c) halo,
 (d) $OR^6$ wherein $R^6$ is
  (1) hydrogen
  (2) $C_{1-3}$ alkyl,
  (3) phenyl-$C_{1-3}$alkyl,

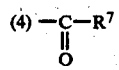

wherein $R^7$ is
 (i) $C_{1-6}$ alkyl
 (ii) $C_{3-6}$ cycloalkyl,
 (iii) phenyl-$C_{1-3}$ alkyl, wherein the phenyl group is unsubstituted or substituted with one or more of halo, $C_{1-3}$ alkyl or $C_{1-3}$ alkoxy,
 (iv) pyridyl-$C_{1-3}$ alkyl,
 (v) furyl-$C_{1-3}$ alkyl,
 (vi) phenyl, either unsubstituted or substituted with one or more of halo, $C_{1-3}$ alkyl or $C_{1-3}$ alkoxy,
 (vii) pyridyl,
 (viii) furyl,
 (ix) —$NR^8R^9$ wherein $R^8$ and $R^9$ are independently hydrogen or $C_{1-3}$ alkyl, or $R^8$ and $R^9$ are joined together to form a heterocycle selected from piperidinyl, morpholinyl, piperazinyl and N-$C_{1-3}$ alkylpiperazinyl; and
$R^5$ is hydrogen, $C_{1-3}$ alkyl or phenyl.

24. The method of claim 23 for treating Parkinsonism which comprises the administration to a patient in need of such treatment of an effective amount of an art-recognized antiparkinsonism agent, and of an effective amount of a compound of structural formula:

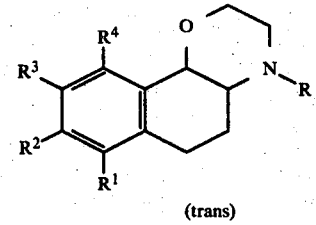
(trans)

with positive or zero optical activity, or a pharmaceutically acceptable salt thereof, wherein:
R is
 (a) hydrogen,
 (b) $C_{1-4}$ alkyl,
 (c) $C_{2-5}$ alkenyl, or
 (d) phenyl-$C_{1-4}$ alkyl; and
$R^1$, $R^2$, $R^3$ and $R^4$ are independently:
 (a) hydrogen,
 (b) $C_{1-3}$ alkoxy,
 (c) hydroxy,
 (d) $C_{1-4}$alkyl,
 (e) halo,
 (f) phenyl-$C_{1-3}$alkoxy, or
 (g) adjacent R groups taken together are methylenedioxy.

25. The method of claim 24 wherein the compound has positive optical activity.

26. The method of claims 23, 24 or 25 wherein R is $C_{1-4}$ alkyl and one or more of $R^1$, $R^2$, $R^3$ and $R^4$ is hydroxy or methoxy.

27. The method of claim 23, 24 or 25, wherein R is n-propyl, $R^3$ is hydroxy or methoxy and $R^1$, $R^2$ and $R^4$ are hydrogen.

28. A method of treating depression which comprises the administration to a patient in need of such treatment of an effective amount of a compound of structural formula:

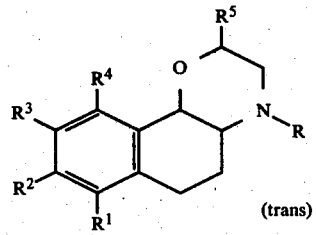
(trans)

with negative or zero optical activity, or a pharmaceutically acceptable salt thereof, wherein:
R is
 (a) hydrogen,
 (b) $C_{1-4}$ alkyl,
 (c) $C_{2-5}$ alkenyl,
 (d) phenyl-$C_{1-4}$ alkyl; and
$R^1$, $R^2$, $R^3$ and $R^4$ are independently:
 (a) hydrogen,
 (b) $C_{1-4}$ alkyl,
 (c) halo,
 (d) $OR^6$ wherein $R^6$ is
  (1) hydrogen
  (2) $C_{1-3}$ alkyl,
  (3) phenyl-$C_{1-3}$alkyl, (4) $-\underset{\underset{O}{\|}}{C}-R^7$ wherein $R^7$ is
(i) $C_{1-6}$ alkyl
(ii) $C_{3-6}$ cycloalkyl,
(iii) phenyl-$C_{1-3}$ alkyl, wherein the phenyl group is unsubstituted or substituted with one or more of halo, $C_{1-3}$ alkyl or $C_{1-3}$ alkoxy,
(iv) pyridyl-$C_{1-3}$ alkyl,
(v) furyl-$C_{1-3}$ alkyl,
(vi) phenyl, either unsubstituted or substituted with one or more of halo, $C_{1-3}$ alkyl or $C_{1-3}$ alkoxy,
(vii) pyridyl,
(viii) furyl,
(ix) $-NR^8R^9$ wherein $R^8$ and $R^9$ are independently hydrogen or $C_{1-3}$ alkyl, or $R^8$ and $R^9$ are joined together to form a heterocycle selected from piperidinyl, morpholinyl, piperazinyl and N-$C_{1-3}$ alkylpiperazinyl; and $R^5$ is hydrogen, $C_{1-3}$ alkyl or phenyl.

29. A method of treating depression which comprises the administration to a patient in need of such treatment of an effective amount of a compound of structural formula:

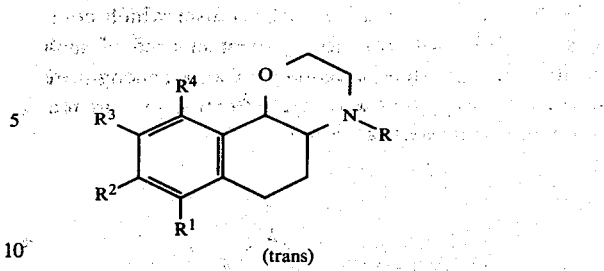
(trans)

with negative or zero optical activity, or a pharmaceutically acceptable salt thereof, wherein:
or a pharmaceutically acceptable salt therof, wherein:
R is
(a) hydrogen,
(b) $C_{1-4}$ alkyl,
(c) $C_{2-5}$ alkenyl, or
(d) phenyl-$C_{1-4}$ alkyl; and
$R^1$, $R^2$, $R^3$ and $R^4$ are independently:
(a) hydrogen,
(b) $C_{1-3}$ alkoxy,
(c) hydroxy,
(d) $C_{1-4}$ alkyl,
(e) halo,
(f) phenyl-$C_{1-3}$ alkoxy, or
(g) adjacent R groups taken together are methylenedioxy.

30. The method of claim 29 wherein the compound has negative optical activity.

31. The method of claims 28, 29 or 30 wherein R is $C_{1-4}$ alkyl and one or more of $R^1$, $R^2$, $R^3$ and $R^4$ is hydrogen or methoxy.

32. The method of claim 28, 29 or 30, wherein R is n-propyl, $R^3$ is hydroxy or methoxy and $R^1$, $R^2$ and $R^4$ are hydrogen.

* * * * *